United States Patent
Oh et al.

(10) Patent No.: US 8,973,190 B2
(45) Date of Patent: Mar. 10, 2015

(54) FOAM WITH GREEN TEA ADDITIVE FOR FOAM MATTRESSES, PILLOWS AND CUSHIONS

(75) Inventors: Suk Kan Oh, Xiamen (CN); Youn Jae Lee, Pleasanton, CA (US)

(73) Assignee: Zinus, Inc., San Leandro, CA (US)

( * ) Notice: Subject to any disclaimer, the term of this patent is extended or adjusted under 35 U.S.C. 154(b) by 668 days.

(21) Appl. No.: 12/661,564

(22) Filed: Mar. 19, 2010

(65) Prior Publication Data
US 2010/0175193 A1    Jul. 15, 2010

Related U.S. Application Data

(63) Continuation-in-part of application No. 12/589,961, filed on Oct. 30, 2009, which is a continuation of application No. 12/214,080, filed on Jun. 16, 2008, now Pat. No. 7,624,465, application No. 12/661,564, which is a continuation-in-part of application No. 12/589,840, filed on Oct. 28, 2009, now abandoned.

(30) Foreign Application Priority Data

Jun. 18, 2007 (CN) .......................... 2007 1 0009121

(51) Int. Cl.
| | |
|---|---|
| *A47G 9/10* | (2006.01) |
| *A47C 27/14* | (2006.01) |
| *A47C 27/15* | (2006.01) |
| *A47C 31/00* | (2006.01) |
| *A47G 9/00* | (2006.01) |
| *A61F 5/56* | (2006.01) |
| *C08H 8/00* | (2010.01) |
| *C08L 97/02* | (2006.01) |
| *C08J 9/00* | (2006.01) |

(52) U.S. Cl.
CPC ................ *A47C 27/14* (2013.01); *A47C 27/15* (2013.01); *A47C 31/004* (2013.01); *A47C 31/007* (2013.01); *A47G 9/007* (2013.01); *A61F 5/56* (2013.01); *C08H 8/00* (2013.01); *C08L 97/02* (2013.01); *C08J 9/0004* (2013.01); *A47G 9/109* (2013.01); *A47G 2009/1018* (2013.01)
USPC ....................................... 5/636; 5/639; 5/640

(58) Field of Classification Search
USPC ............. 5/636, 638, 639, 640, 641, 643, 922, 5/951, 948
See application file for complete search history.

(56) References Cited

U.S. PATENT DOCUMENTS

| | | | |
|---|---|---|---|
| 4,996,734 A * | 3/1991 | Rowe ................................ | 5/636 |
| 5,781,947 A | 7/1998 | Sramek ............................ | 5/636 |
| 5,926,880 A | 7/1999 | Sramek ............................ | 5/636 |

(Continued)

*Primary Examiner* — Michael Trettel
(74) *Attorney, Agent, or Firm* — Imperium Patent Works; Darien K. Wallace

(57) ABSTRACT

A method of making foam imparts antimicrobial and antiodorant qualities to the foam. Green tea powder is added to the polyol raw materials for making memory foam. The green tea memory foam is used to make pillows, cushions and mattresses. Green tea foam in the top layer of a mattress acts as an antiodorant such that less of the chemical smell of the memory foam is perceived by the user. In addition, the bacteria and mold that would otherwise develop in the moist warmer sleeping environment on memory foam are killed by the green tea additive to the foam. Measurable antimicrobial and antiodorant qualities in the green tea foam are achievable by adding green tea powder constituting less than 2% of the weight of the resulting green tea foam. A neck-support contour pillow is made using memory foam that contains green tea and a green dye.

18 Claims, 6 Drawing Sheets

(56) References Cited

U.S. PATENT DOCUMENTS

| | | | |
|---|---|---|---|
| 6,006,380 A | 12/1999 | Sramek | 5/636 |
| 6,042,604 A * | 3/2000 | Gennetti | 607/108 |
| 6,151,733 A | 11/2000 | Takashima | 5/636 |
| 6,173,675 B1 | 1/2001 | Licciardo | 119/28.5 |
| 6,430,764 B1 | 8/2002 | Peters | 5/641 |
| 6,869,681 B2 * | 3/2005 | Okamoto et al. | 428/373 |
| 7,082,633 B1 * | 8/2006 | Maarbjerg | 5/636 |
| 7,255,917 B2 * | 8/2007 | Rochlin et al. | 428/304.4 |
| 2004/0107501 A1 * | 6/2004 | Kancilja et al. | 5/636 |
| 2006/0272098 A1 | 12/2006 | Hochschild | 5/727 |
| 2006/0288490 A1 * | 12/2006 | Mikkelsen et al. | 5/740 |
| 2007/0032561 A1 * | 2/2007 | Lin et al. | 521/131 |
| 2007/0287002 A1 | 12/2007 | Cabados | 428/319.3 |

* cited by examiner

FOAM WITH GREEN TEA ADDITIVE FOR FOAM MATTRESSES, PILLOWS AND CUSHIONS

CROSS REFERENCE TO RELATED APPLICATION

This application is a continuation-in-part of, and claims priority under 35 U.S.C. §120 from, nonprovisional U.S. patent application Ser. No. 12/589,961 entitled "Foam with Green Tea Additive for Foam Mattresses, Pillows and Cushions," filed on Oct. 30, 2009. Application Ser. No. 12/589,961, in turn, is a continuation of U.S. patent application Ser. No. 12/214,080 entitled "Foam with Green Tea Additive for Foam Mattresses, Pillows and Cushions," now U.S. Pat. No. 7,624,465, filed on Jun. 16, 2008. Application Ser. No. 12/214,080, in turn, is a continuation of, and claims the benefit under 35 U.S.C. §119 from, Chinese Patent Application No. 200710009121.2, filed in China on Jun. 18, 2007. This application is also a continuation-in-part of, and claims priority under 35 U.S.C. §120 from, nonprovisional U.S. patent application Ser. No. 12/589,840 entitled "Anti-Snore Neck-Support Contour Pillow," filed on Oct. 28, 2009 now abandoned. The subject matter of each of the aforementioned patent documents is incorporated herein by reference.

TECHNICAL FIELD

The described embodiments relate to foam additives, and more particularly to adding green tea to foam used in bedding products.

BACKGROUND INFORMATION

Due to their good breathability and elasticity characteristics, various foams are used to make items that come into contact with the human body, such as mattresses, pillows and cushions. Throughout one's life, one spends much time asleep. Therefore, the comfort of mattresses and pillows correlates to the degree of healthy recovery of the human body. Thus, pillows and mattresses with therapeutic functions were born. In some cases, raw materials from plants are added to pillow fillings in order to generate a therapeutic function to the human body by taking advantage of the smell generated. It is uncommon, however, to add raw materials from plants into mattresses. Tea leaves have been placed directly into pillow fillings because of perceived ability of tea leaves to brighten the eyesight, refresh the brain and resist radiation.

Placing crushed tea leaves in a pillow case or mattress covering, however, detracts from the comfort of the pillow or mattress. In addition, as mattresses, pillows and cushions are used, the tea leaves are crushed and tea leaf dust is formed. The tea leave dust then seeps out of the pillow case or mattress covering.

A manufacturing process is sought for allowing users of mattresses, pillows and cushions to take advantage of the benefits of tea leaves, but that also avoids the disadvantages of leaking tea leaf dust.

SUMMARY

A method of making foam imparts antimicrobial and antiodorant qualities to the foam.

Polyol raw materials and a green dye are mixed together, and then a silicone surfactant is added. The polyol raw materials include a memory foam polyol, a polyol for polyurethane and a polymer polyol. The silicone surfactant is mixed with the polyol raw materials. Green tea powder is then added to the green polyol raw materials. Water and the catalyst isocyanate are added to the green polyol raw materials to make green tea foam.

The green tea memory foam is used to make pillows, cushions and mattresses. Bacteria, mites and mold that live in the fabric of a pillow case are killed when they come into contact with the green tea foam. In addition, the green tea additive decreases the smell of the memory foam chemicals in the memory foam pillow.

Green tea foam in the top layer of a mattress acts as an antiodorant such that less of the chemical smell of the memory foam is perceived by the user. In addition, people sleep warmer and tend to perspire on memory foam. The bacteria and mold that are attracted to the warm moist environment on memory foam are killed by the green tea additive to the foam. Measurable antimicrobial and antiodorant qualities in the green tea foam are achievable by adding green tea powder constituting less than 2% of the weight of the resulting green tea foam.

Green tea powder or extract provides a natural, plant-based means for reducing the chemical odor of foam mattresses.

In another embodiment, the molded foam of the body of an anti-snore neck-support pillow contains green tea and a green dye. The anti-snore neck-support pillow includes a contoured body of molded memory foam and a fabric covering that encloses the body. The molded foam body includes a front portion with a first thickness, a back portion with a second thickness, and a middle portion with a third thickness. The third thickness is thinner than both the first thickness and the second thickness. The top surface of the body has a concave curve between the front portion and the back portion. The molded foam of the body conforms around a foam support member that is disposed horizontally within the front portion. A plurality of vertical holes pass completely through the middle portion of the molded foam body.

The support member is made of foam having a hardness greater than that of the molded foam of the body. The molded foam body has a substantially flat bottom surface with an indentation located opposite the concave curve of the top surface. The support member provides a means for increasing the firmness of the foam in the front portion of the body, whereas the vertical holes and the indentation provide a means for decreasing the firmness of the body of molded foam in the middle portion. When the support member lifts the user's neck, and the holes and indentation allow the user's head to sink into the middle portion of the body, the user's head is tilted back, which opens the user's airways.

In yet another embodiment, the body of molded foam of an anti-snore pillow contains green tea and a green dye. The body of the pillow includes a front portion that has a first thickness, a back portion that has a second thickness, and a middle portion that has a third thickness. The third thickness is thinner than both the first thickness and the second thickness. The anti-snore pillow also has a right foam support and a left foam support disposed under the body. A groove is formed under the body between the right foam support and the left foam support. A plurality of shims are disposed under the body at one end of the groove between the right foam support and the left foam support and provide support for a user's neck. A fabric covering encloses the body, the right foam support, the left foam support and the plurality of shims.

Further details and embodiments are described in the detailed description below. This summary does not purport to define the invention. The invention is defined by the claims.

BRIEF DESCRIPTION OF THE DRAWINGS

The accompanying drawings illustrate embodiments of the invention.

DETAILED DESCRIPTION

The present invention provides a method of manufacturing a foam that has the therapeutic functions of the tea plant (*Camellia sinensis*) and that can be made into a pillow, cushion or mattress. The method provides a delivery mechanism for delivering green tea along with bedding products. In the manufacturing method, ground tea leaves or tea stems are added to the raw materials used to make the foam, and the green tea powder becomes evenly dispersed in the foam as the foam sets up.

Figure 1:
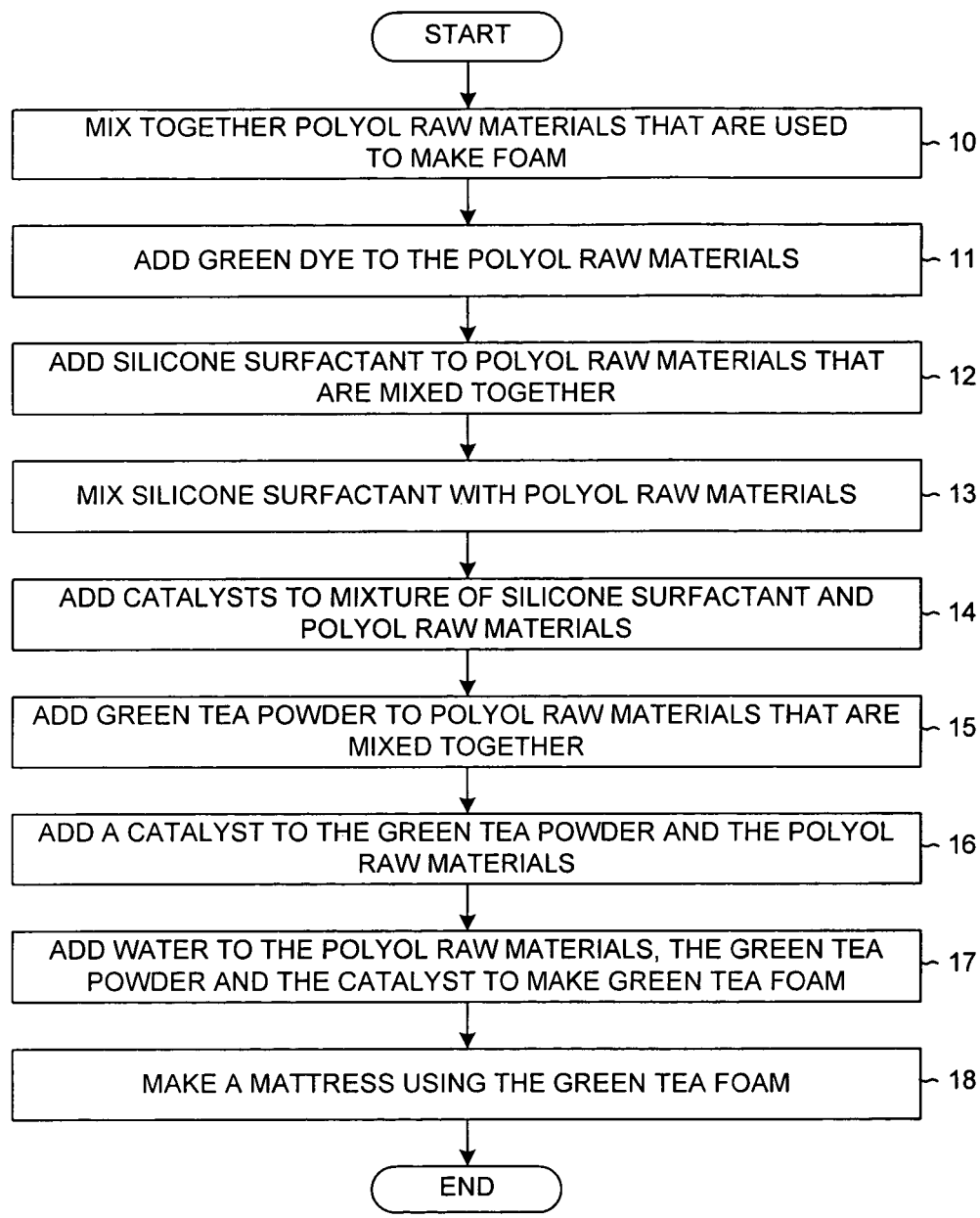
FIG. 1 is a flowchart illustrating steps of a method for controlling bacterial and germ growth and for absorbing odors in foam.

FIG. 1 is a flowchart illustrating steps 10-18 of a method for controlling bacterial, germ and mold growth and for absorbing odors in foam. In one embodiment, antimicrobial and antiodorant qualities are imparted to polyurethane foam used to make a mattress. The polyurethane foam is visco-elastic or "memory" foam and is used to make the top layer of the mattress on which a user directly rests.

In a first step 10, three different polyol raw materials are mixed together. To make memory foam, a memory foam polyol is mixed together with a polyol for polyurethane and a polymer polyol. In one embodiment, the relative volumes of (i) the memory foam polyol, (ii) the polyol for polyurethane and (iii) a polymer polyol are 2:1:1. Different ratios result in memory foam with different firmness and density. The three polyols are mixed for about 30 minutes.

In a step 11, a green dye is added to the mixture of polyol raw materials. The green tea powder added later is actually yellow and does not impart a green color to the foam. Adding green dye to make the top foam layer green adds to consumer awareness that the mattress contains green tea.

In a step 12, a silicone surfactant is added to the green mixture of polyol raw materials. Silicone surfactant in the amount of about 1% by weight is added to the colored mixture of polyol raw materials.

In a step 13, the silicone surfactant and the mixture of polyol raw materials are mixed. The silicone surfactant creates a consistent foaming reaction between the different chemical functional groups of the molecules of the three different polyols. The silicone surfactant promotes a stable rising of the foam and a stable cell structure of the foam. Creating a homogeneous polyurethane reaction allows the green tea powder added later to be more evenly disbursed throughout the foam. A homogeneous polyurethane reaction also promotes dispersion of the catalysts that are added later. The silicone surfactant is a combination of molecules having hydrophobic and hydrophilic functional groups. There are various silicone surfactants that are more or less hydrophobic or hydrophilic. In one embodiment, a more hydrophilic silicone surfactant is used to accommodate the green tea powder. For example, a silicone surfactant made by the General Electric company can be used.

In a step 14, catalysts are added to the mixture of silicone surfactant and the polyol raw materials. In one embodiment, three catalysts are added: two tin jelling catalysts and one amine foam-blowing catalyst. The catalysts, a physical property promoter, the silicone surfactant and the polyol raw materials are mixed for about an hour. The catalysts accelerate the chemical foaming reaction once the isocyanate and water are added.

In a step 15, green tea powder is added to the mixture from step 14, and the mixture is agitated for about an additional thirty minutes. Measurable antimicrobial and antiodorant qualities in the green tea foam are achievable by adding green tea powder constituting even less than 2% of the weight of the resulting green tea foam. In one embodiment, green tea powder in an amount of about 0.1% of the total weight of the mixture from step 14 is added in step 15. In another embodiment, the volume of the tea leaf powder or tea water solution accounts for about 1% to 15% of the total volume of the polyol raw materials. Although only a small relative amount of green tea powder is added, the amount of silicone surfactant added in step 13 should be increased to compensate for the weight of the green tea powder. In another embodiment, instead of green tea powder, a green tea water solution is added to the mixture of step 14.

In a step 16, the catalyst isocyanate is added to the green tea mixture of step 15. Isocyanate in the presence of water begins the reaction that forms polyolurethane foam from the mixture of step 15. The catalysts of step 14 accelerate the reaction, whereas the reaction will not take place without the catalyst isocyanate.

In a step 17, water is added to the green tea mixture of step 15 and the isocyanate. In one embodiment, less than one percent water by volume is added to the mixture of step 15. When the water is added, the green tea forms within about three minutes. It takes about 24 hours, however, for all of the molecules of the raw materials to undergo the chemical reaction. During the chemical reaction, heat is generated inside the foam. During the 24-hour curing time, this heat and much of the foam smell dissipates.

Where a green tea water solution is added in step 15, the chemical reaction the forms foam begins as soon as the isocyanate is added in step 16. Adding additional water in step 17 is not necessary if sufficient water is added in step 15 in the form of the green tea water solution. In another embodiment, isocyanate and water are together injected into the mixture of step 15 as the mixture flows past into an agitating head of a foam-making machine.

By adding the green tea ingredients directly into the raw materials of the foam that is tailored into a pillow, cushion or mattress, the need for a separate structure in the pillow, cushion or mattress to accommodate the green tea ingredients is avoided. The foam containing green tea ingredients thus achieves a therapeutic function to the human body and imparts to the foam a resistance to insects, bacteria and mold.

In another embodiment, the volume of the aforementioned tea leaf powder or green tea water solution account for between 1% to 15% of the entire volume of the foam raw materials. Either the 1% to 15% tea leaves or stems are added into the already foaming raw materials of the foam, or 1% to 15% tea leaf powder or tea leaf water solution are added before the polyol raw materials are foamed and shaped in a mechanical foaming device and shaped into a foam with tea ingredients. Tea leaves, tea stems or green tea powder are evenly distributed in the foam to provide a therapeutic function.

In a step 18, the green tea foam is used to make a pillow, cushion or mattress.

Figure 2:
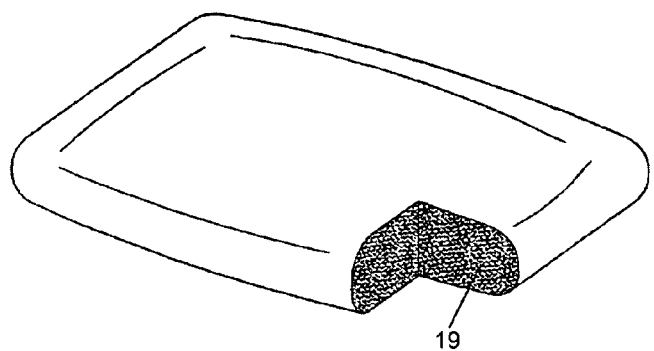
FIG. 2 illustrates green tea foam that has been shaped directly into a pillow or cushion.

FIG. 2 illustrates green tea foam manufactured according to the method of FIG. 1 that has been shaped directly into a pillow or cushion. FIG. 2 shows that tea leaves or stems 19 are evenly distributed in the green tea foam. Mites and mold that might otherwise accumulate in the fabric of a pillow case are controlled in proximity to the green tea foam. In addition, the green tea additive decreases the smell of the memory foam chemicals in the memory foam pillow. This solves one of the main consumer complaints of pillows made from memory foam. There is no need to place a separate structure in the pillow of FIG. 2 to accommodate ground tea leaves or stems. Thus, the manufacturing process of the pillow is simpler and cheaper than including a receptacle for tea leaves. The evenly distributed tea leaves or stems are resistant to insects, bacteria and mold.

Figure 3:
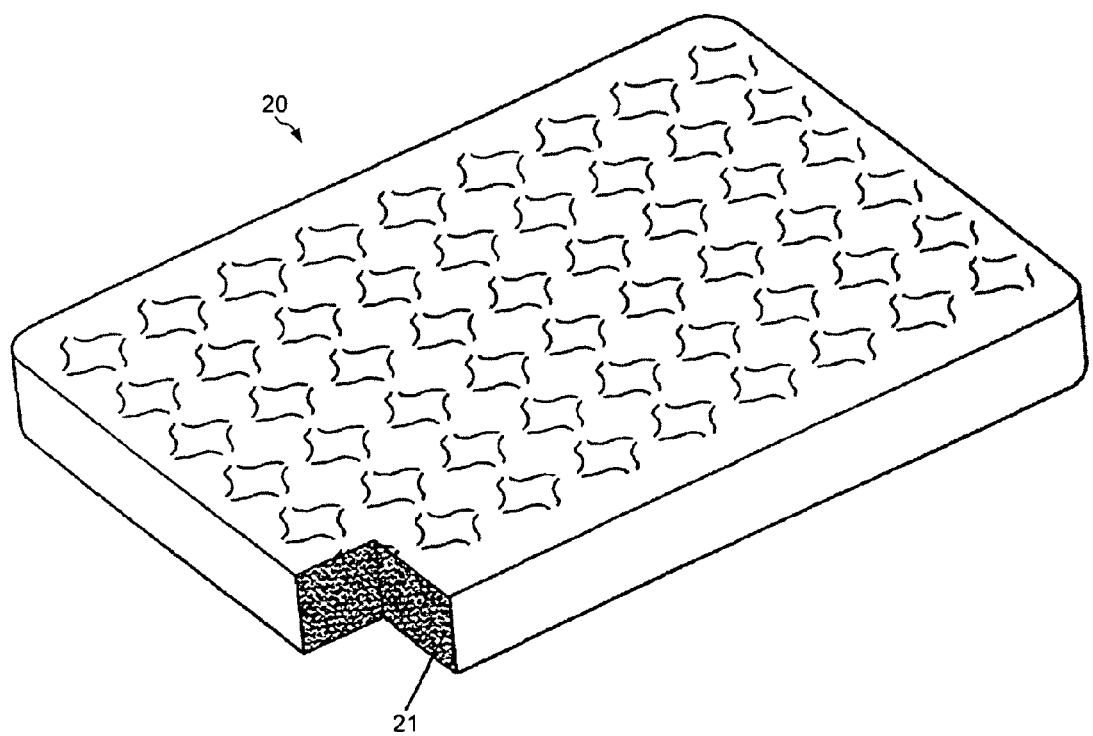
FIG. 3 shows a mattress made from green tea foam in which the tea is evenly distributed throughout the foam.

FIG. 3 shows a mattress 20 made from the green tea foam manufactured according to the method of FIG. 1. Tea leaves or stems 21 are evenly distributed in the green tea foam of mattress 20.

Figure 4:
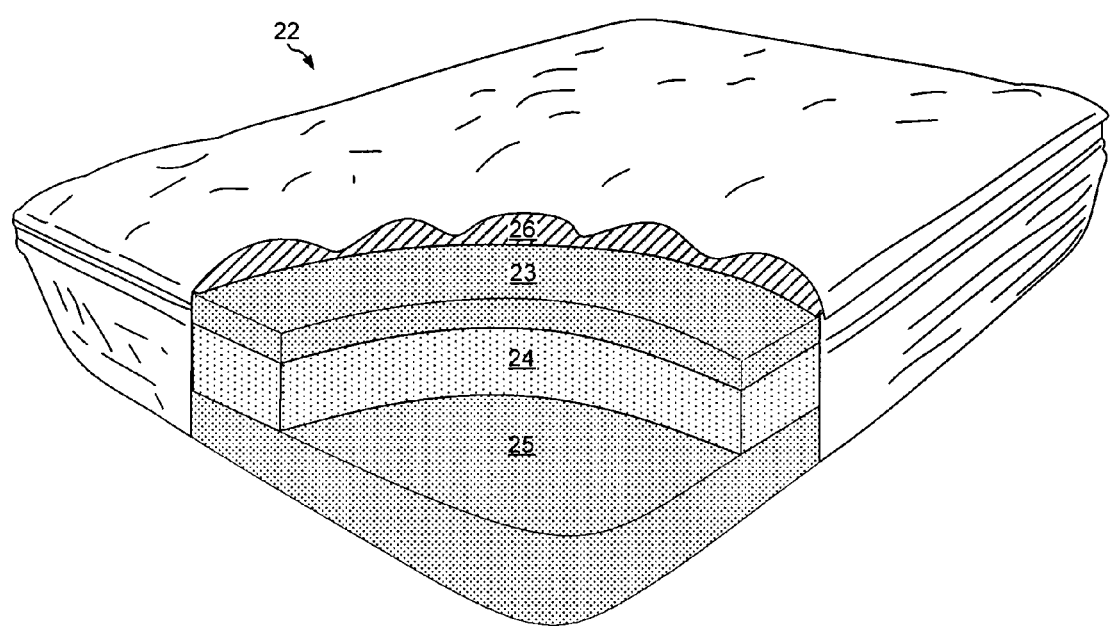
FIG. 4 shows a multi-layered foam mattress in which only the top foam layer contains green tea and is colored green.

FIG. 4 shows a mattress 22 made from multiple layers 23-25 of foam. In one embodiment, only the top foam layer 23 of the mattress contains green tea and is colored green. A person using mattress 22 lies directly on layer 23 through a thin quilted fiber padding 26 of the mattress cover. The green tea in top layer 23 acts as an antiodorant such that less of the chemical smell of the memory foam is perceived by the user. In addition, people tend to perspire more while sleeping on memory foam. The bacteria and mold that would otherwise develop in the moist environment of the memory foam are killed by the green tea additive to the foam. The green-colored top layer is helpful in marketing the mattress where a cutaway display sample is used in a showroom. Top foam layer 23 is made of green tea memory foam, whereas bottom layer 26 is made of rigid high density HD foam. Middle layer 24 is made of chopped up chunks of memory foam glued together with pieces of regular polyurethane foam to prevent a user from "bottoming out" on harder bottom layer 25. Optionally, all three layers 23-25 of foam include green tea powder.

Figure 5:
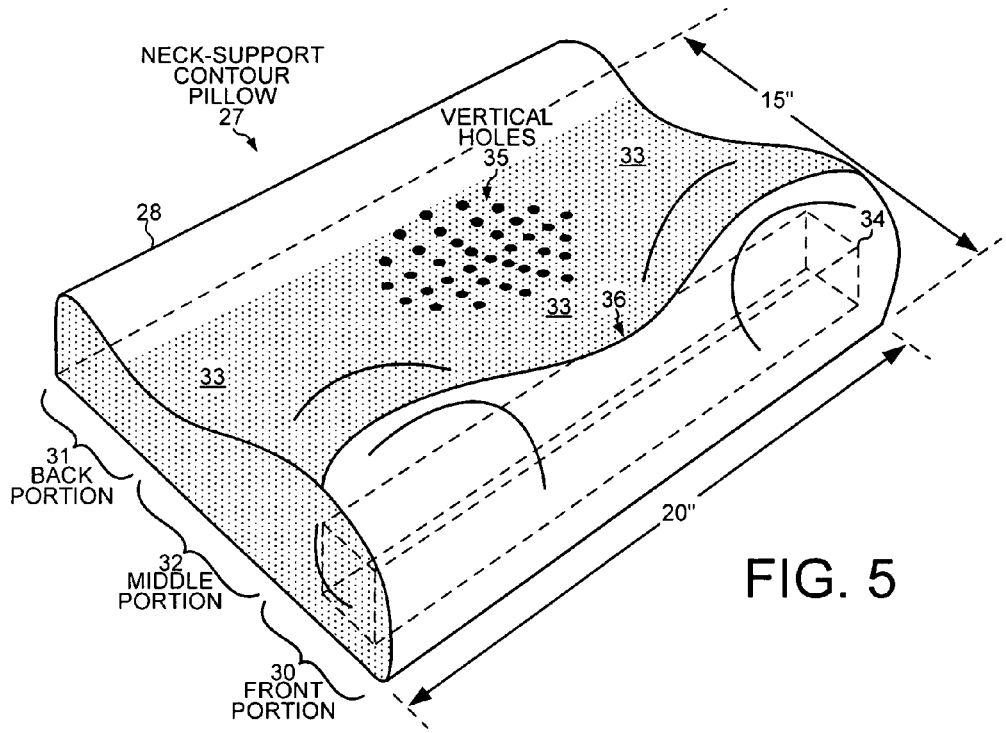
FIG. 5 is a perspective view of another embodiment of a pillow made of foam that contains green tea.

FIG. 5 shows another embodiment of a pillow 27 made of foam that contains green tea. Neck-support contour pillow 27 has a contoured configuration that both supports the neck and tilts back the head of a user lying supine (face up) on the pillow. Neck-support contour pillow 27 includes a body 28 of molded foam and a fabric covering 29 that encloses the body. Fabric covering 29 is removed in FIG. 5 (see FIG. 7). In one embodiment, body 28 of molded foam is about twenty inches wide and fifteen inches long. Body 28 has a front portion 30 with a first thickness, a back portion 31 with a second thickness and a middle portion 32 with a third thickness. In the embodiment of FIG. 5, the second thickness is thinner than the first thickness and thicker than the third thickness. In an alternate embodiment, the first thickness approximately equals the second thickness, and the third thickness is thinner than both the first thickness and the second thickness. The front portion in FIG. 5 is about 3.5 inches thick. Body 28 has a top surface 33 with a concave curve between front portion 30 and back portion 31.

A support member 34 is disposed horizontally within front portion 30 of body 28. Support member 34 is about eighteen inches long, 1.75 inches wide, and 2.5 inches tall. All six sides of support member 34 are planar and rectangular. The molded foam of body 28 conforms around support member 34. In one embodiment, body 28 is made of visco-elastic polyurethane foam that is poured into a mold and thereby molded into the form of contoured pillow 27. The molded memory foam of body 28 has a hardness corresponding to an indentation load deflection (ILD) in the range of 6-10. The ILD is a measure of the contacting hardness of the foam, which is the force required to compress the foam by a specified percentage in a predetermined manner. A harder foam exhibits a higher ILD. In one embodiment, support member 34 is also made of memory foam. Alternatively, support member 34 is made of high-density polyurethane (HD) foam. Support member 34 is foam cut from a foam slab having an ILD in the range of 12-14. Support member 34 is made of foam having a density of about four pounds per cubic foot, and body 28 is made of foam having a density of about 3.5 pounds per cubic foot. Some types of memory foam tend to become softer in the presence of body heat. When foam is used for support member 34 that does not become softer with body heat, the support provided by support member 34 does not sag during the night as pillow 27 warms up. In yet another embodiment, support member 34 is made of pliable plastic.

FIG. 5 shows a plurality of distributed cylindrical vertical holes 35 that pass completely through body 28 of molded foam at the center of middle portion 32 of body 28. In an alternative embodiment, vertical holes 35 are countersunk holes from the bottom surface of body 28 and do not pass completely through top surface 33. The center of middle portion 32 corresponds to the contact position between pillow 27 and the back of the head of a person reclining thereon. The center of front portion 30 corresponds to the contact position between pillow 27 and the neck of a person reclining thereon. Vertical holes 35 are punched through body 28 after the memory foam has already been molded. Alternatively, holes 35 may be formed through a single step of the foam molding process in which a plurality of cylinders are provided inside the foam mold. Making holes 35 using a foam mold saves on raw materials for the foam as foam is never formed in the area of the holes and is not discarded as when the holes are punched out. Yet another alternative method of making holes 35 is to drill into the molded foam with rotating bits.

Holes 35 may have circular or non-circular cross sections, such as ovals, polygons or triangles. By providing holes 35 in the center of middle portion 32, the amplitude of deformation of the foam is increased so as to decrease the contacting hardness of the foam. The softness of the center of middle portion 32 can be adjusted by varying the spacing and diameter of the holes 35 and by varying the depth of the holes where the holes are not through holes. For example, the holes can be spaced farther apart to increase the hardness. By decreasing the contacting hardness at the center of middle portion 32, the user's head sinks deeper into pillow 27. At the same time, support member 34 with firmer and higher-density foam than the molded foam of body 28 provides higher support for the user's neck, which allows the user's head to tilt back into pillow 27 and which opens the user's airways. Existing anti-snore pillows that provide inadequate support beneath the neck and that do not sufficiently tilt back the head cause the user to sleep with his chin close to his chest, which may result in a restricted airway. Sleeping with a restricted airway may cause snoring and lead to obstructive sleep apnea.

Body 28 of pillow 27 has a contour 36 in the center of front portion 30. Contour 36 is a concave curve in the center of the neck-support region that reduces side-to-side movement of the head of the user. The user's neck is relaxed during sleeping because the neck need not maintain the face-up orientation of the head. In addition, because support member 34 underneath contour 36 raises the neck, and vertical holes 35 and an indentation 37 on the bottom surface 38 allow the head to sink into body 28 and tilt back, the user's airways are pulled open, and obstructive sleep apnea is reduced.

Figure 6:
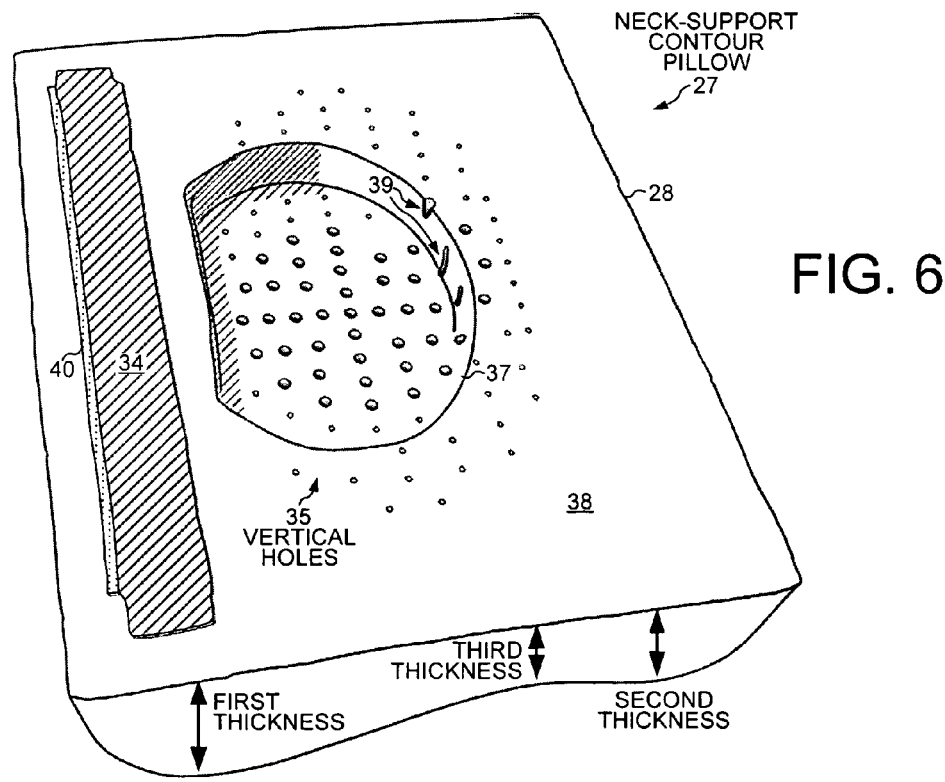
FIG. 6 is a bottom perspective view of the neck-support contour pillow of FIG. 6.

FIG. 6 shows a bottom perspective view of body 28 of molded foam. Body 28 has a substantially flat bottom surface 38 with an indentation 37 located at the center and opposite the concave curve of top surface 33. Most of vertical holes 28 exit bottom surface 38 inside indentation 37. The holes of the embodiment shown in FIG. 6 were punched through body 28 after the molded foam was formed as opposed to being made during the molding process by cylinders inside the mold. Consequently, FIG. 6 shows that some holes 39 were punched through the side walls of indentation 37. In one embodiment, indentation 37 is about 10.5 inches wide, 6.25 inches long and 1.5 inches deep.

FIG. 6 shows that the molded foam of body 28 conforms around support member 34 only on five of its six sides. Before the liquid mixed raw materials set up as the molded foam of body 28, the liquid raw materials flow around five of the six sides of support member 34. The liquid raw materials do not flow onto the surface of support member 34 that is shown in FIG. 6 because that surface is removably attached to the inside surface of the lid of the mold. In one embodiment, support member 34 is attached to the lid by needles on the lid that stick down into the foam. When the molded foam of body 28 sets up around support member 34 and the lid of the mold is removed, the needles pulls away from support member 34. FIG. 6 also shows a narrow strip 40 parallel to support member 34. Strip 40 is molded foam from which the outer skin has been torn away when the lid of the mold was removed. The cells of the memory foam can be seen in strip 40, whereas the other outer surfaces of the molded foam are covered by a smooth skin that forms adjacent to the inner surfaces of the mold.

FIG. 6 shows that there are two sizes of the vertical holes 35. The holes at the center of the matrix of holes have a larger diameter than the holes towards the outside of the matrix of holes. Consequently, the ILD of the structure of body 28 is lower at the center of the matrix of holes than towards the outside of the matrix of holes. Moreover, the thickness of foam between indentation 37 and the concave curve of top surface 33 is thinner than elsewhere. Thus, the firmness of body 28 above indentation 37 and at the center of the matrix of holes 35 is further reduced. The combined effect of the dual sized holes 35 and indentation 37 causes the user's head to tilt back into the correct location on top surface 33.

Figure 7:
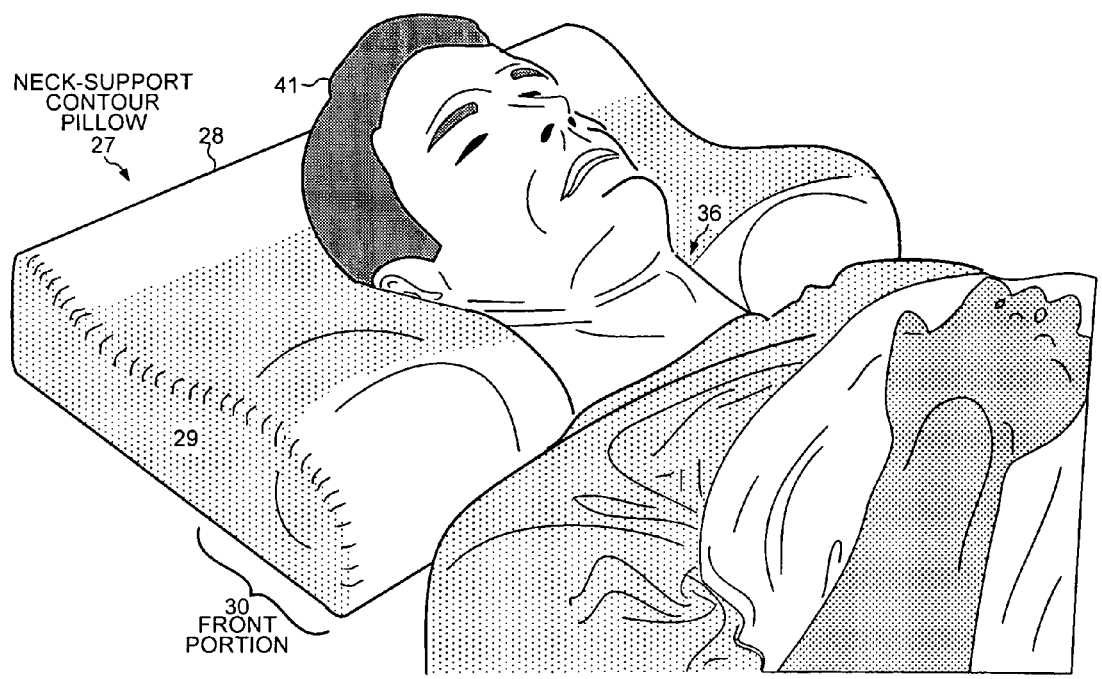
FIG. 7 is another perspective view of the pillow of FIG. 6 with the head of a user tilted back and the user's neck supported by a support member.

FIG. 7 shows another perspective view of neck-support contour pillow 27 with the head 41 of a user tilted back and the user's neck supported in contour 36 by support member 34. The green tea in the molded foam of body 28 kills the mites and mold that might otherwise accumulate in the fabric covering 29 of a pillow case. No receptacle for ground up tea leaves is required around the pillow because the green tea is integrated into the foam. The evenly distributed green tea throughout top surface 33 better kills insects, bacteria and mold. In addition, the green tea additive decreases the smell of the memory foam chemicals in body 28 of molded foam and thereby reduces one of the main consumer complaints of pillows made from memory foam. The vertical holes 35 and indentation 37 allow the user's head 41 to sink deeper into pillow 27. At the same time, support member 34 with firmer and higher-density foam provides more support for the user's neck and causes the user's head 41 to tilt back into pillow 27 and the user's airways to open.

A green dye is added to the molded foam of body 28 in order to impart a green color to the foam. The 2% green tea added to the foam is insufficient to color the foam and in any event is colored yellow instead of green. Adding green dye to make pillow body 28 green adds to consumer awareness that pillow 27 contains green tea. The green-colored memory foam is helpful in marketing pillow 27 where the fabric covering 29 is left partially unzipped in the packaging on the store shelf to expose the green-colored foam.

Figure 8:
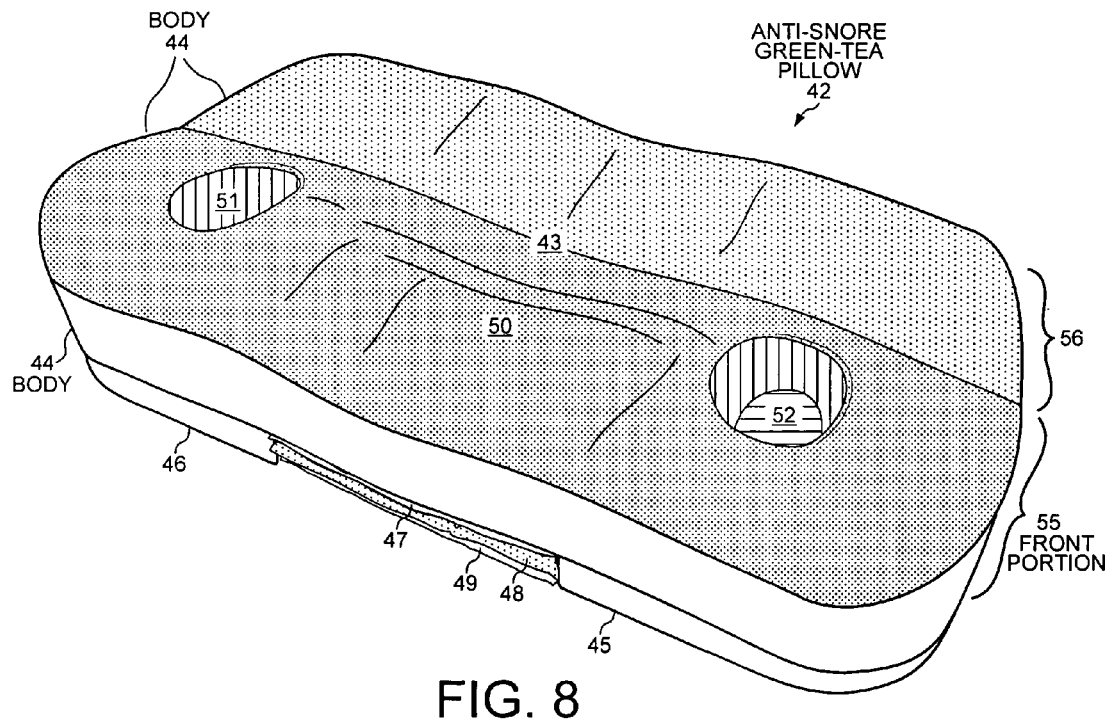
FIG. 8 is a perspective view of yet another embodiment of a pillow made of foam that contains green tea.

FIG. 8 shows yet another embodiment of a pillow 42 made of foam that contains green tea and that has a predetermined contoured shape designed to prevent snoring. Green-tea contour pillow 42 also tilts the user's head back such that the user's airways remain open. FIG. 8 shows anti-snore, green-tea pillow 42 with the cloth covering removed. Pillow 42 reduces snoring by supporting the neck of a user lying face up such that the user's head tilts back into a depression 43. Pillow 42 includes a pillow body 44 of molded foam, a right foam support 45, a left foam support 46, and a plurality of shims 47-49 located under a neck support region 50. Pillow body 44 includes a right ear depression 51 and a left ear depression 52 for receiving the user's ears when the user is lying on his side. The molded foam of body 44 contains green tea in the form of a powder of green tea leaves, a powder of green tea stems or a water solution of green tea extract.

Figure 9:
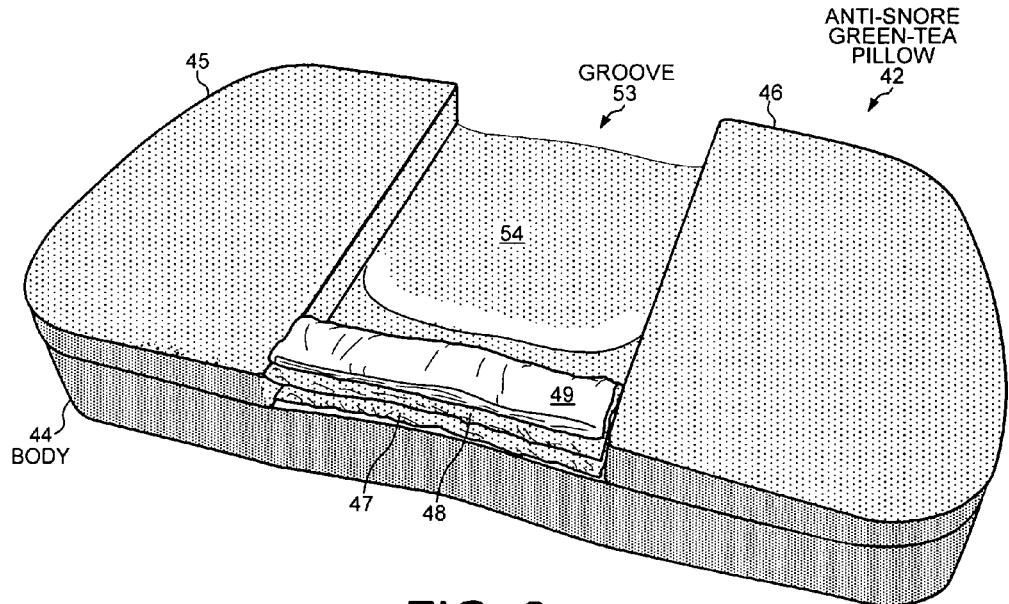
FIG. 9 is a bottom perspective view of the anti-snore, green-tea pillow of FIG. 8.

FIG. 9 shows a bottom view of green-tea pillow 42. Each of right foam support 45 and left foam support 46 is a slab of foam that is glued to the bottom of pillow body 44. Each of the foam supports 45-46 covers about one third of the bottom area of pillow body 44, leaving the central one third uncovered. Foam supports 45-46 form a groove 53 through the central uncovered area of the bottom area of pillow body 44. FIG. 9 shows an indentation 54 in the molded foam of pillow body 44 that deepens groove 53. The shims 47-49 are located at one end of groove 53 beneath neck support region 50. The shims 47-49 are strips of foam covered by cloth and are attached to each other and to pillow body 44 by adhesive tape or by fabric hook-and-loop fasteners, such as Velcro®. By adding fewer or more shims, the neck support can be adjusted. In any event, the plurality of shims extend from the resting surface of pillow 42 to the bottom surface of body 44. In the most common use, the resting surface of pillow 42 is the top surface of a mattress. Because groove 53 is not supported by shims, the user's head depresses into depression 43.

In another embodiment, pillow body 44 is made of two types of green-tea memory foam. A front portion 55 of pillow body 44 is made of a firmer and higher-density foam that better supports the user's neck, as shown in FIG. 8. A back portion 56 of the pillow body 44 is made of a softer and lower-density foam that allows the user's head to sink deeper into depression 43.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A pillow comprising:
   a body of molded foam, wherein the molded foam is memory foam and contains green tea and a green dye, wherein a front portion of the body has a first thickness, a back portion of the body has a second thickness, and a middle portion of the body has a third thickness, and wherein the third thickness is thinner than both the first thickness and the second thickness;
   a right foam support disposed under the body;

a left foam support disposed under the body, wherein a groove is formed under the body between the right foam support and the left foam support;

a plurality of shims disposed under the body at one end of the groove between the right foam support and the left foam support; and a fabric covering that encloses the body, the right foam support, the left foam support and the plurality of shims.

2. The pillow of claim 1, wherein the green tea is in a form taken from the group consisting of: a powder of green tea leaves, a powder of green tea stems and a water solution of green tea extract.

3. The pillow of claim 1, wherein the molded foam is visco-elastic foam.

4. The pillow of claim 1, wherein the green tea constitutes less than 2% of the weight of the molded foam.

5. The pillow of claim 1, wherein the body has a bottom surface, wherein a depression is formed at the middle portion of the body opposite the bottom surface, and wherein the right foam support is glued to the bottom surface of the body.

6. The pillow of claim 1, wherein the body has a bottom surface, wherein the right foam support and the left foam support the bottom surface of the body above a resting surface, and wherein the plurality of shims extend from the resting surface to the bottom surface.

7. The pillow of claim 1, wherein the body has a top surface, and wherein a depression is formed in the top surface at the middle portion of the body above the groove.

8. The pillow of claim 1, wherein the body has a top surface, and wherein a right ear depression is located in the top surface above the left foam support.

9. The pillow of claim 1, wherein the plurality of shims are strips of foam covered by cloth that are attached to each other and to the body by fabric hook-and-loop fasteners.

10. A pillow comprising:
a body of molded foam, wherein the molded foam is memory foam and contains green tea and a green dye, wherein a front portion of the body has a first thickness, a back portion of the body has a second thickness, and a middle portion of the body has a third thickness, and wherein the third thickness is thinner than both the first thickness and the second thickness;

a right foam support disposed under the body;

a left foam support disposed under the body, wherein a groove is formed under the body between the right foam support and the left foam support; and means for supporting the body above the groove.

11. The pillow of claim 10, wherein the means supports the body at one end of the groove.

12. The pillow of claim 10, wherein the means is adapted to support a neck of a user lying supine such that a head of the user sinks into the middle portion of the body.

13. The pillow of claim 1, wherein the front portion of the body is made of a firmer and higher-density foam than is the back portion of the body.

14. The pillow of claim 10, wherein the front portion of the body is made of a firmer and higher-density foam than is the back portion of the body.

15. A pillow comprising:
a body of molded foam having a top surface, wherein the top surface has a concave curve between a front portion of the body and a back portion of the body, wherein the molded foam contains green tea and a green dye, and wherein the front portion of the body is made of a firmer and higher-density foam than is the back portion of the body, and wherein the molded foam is memory foam;

a right foam support disposed under the body;

a left foam support disposed under the body, wherein a groove is formed under the body between the right foam support and the left foam support; and a plurality of shims disposed under the body at one end of the groove between the right foam support and the left foam support.

16. The pillow of claim 15, further comprising:
a fabric covering that encloses the body, the right foam support, the left foam support and the plurality of shims.

17. The pillow of claim 15, wherein the plurality of shims are strips of foam covered by cloth that are attached to each other and to the body by fabric hook-and-loop fasteners.

18. The pillow of claim 15, wherein the green tea constitutes less than 2% of the weight of the molded foam.

* * * * *